US011613549B2

(12) United States Patent
Rack et al.

(10) Patent No.: US 11,613,549 B2
(45) Date of Patent: *Mar. 28, 2023

(54) BROMINATION OF PYRIDINE DERIVATIVES

(71) Applicant: BASF SE, Ludwigshafen (DE)

(72) Inventors: Michael Rack, Ludwigshafen (DE);
Bernd Mueller, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/960,192

(22) PCT Filed: Jan. 14, 2019

(86) PCT No.: PCT/EP2019/050794
§ 371 (c)(1),
(2) Date: Jul. 6, 2020

(87) PCT Pub. No.: WO2019/145177
PCT Pub. Date: Aug. 1, 2019

(65) Prior Publication Data
US 2021/0053991 A1 Feb. 25, 2021

(30) Foreign Application Priority Data

Jan. 23, 2018 (EP) .................................. 18152984

(51) Int. Cl.
*C07D 213/61* (2006.01)
*C07F 1/02* (2006.01)
*C07D 217/26* (2006.01)
*C07D 401/04* (2006.01)

(52) U.S. Cl.
CPC .............. *C07F 1/02* (2013.01); *C07D 213/61* (2013.01); *C07D 217/26* (2013.01); *C07D 401/04* (2013.01)

(58) Field of Classification Search
None
See application file for complete search history.

(56) References Cited

U.S. PATENT DOCUMENTS

2014/0194386 A1   7/2014   Burns et al.

FOREIGN PATENT DOCUMENTS

| EP | 2223919 A1 | 9/2010 |
| WO | WO-2006/025979 A2 | 3/2006 |
| WO | WO-2008/070740 A1 | 6/2008 |
| WO | WO-2016/007731 A1 | 1/2016 |
| WO | WO-2017/016915 A1 | 2/2017 |

OTHER PUBLICATIONS

Database Registry Chemical Abstracts Service, Columbus, Ohio, Accession No. RN 117846-56-7, Entered STN: Dec. 2, 1988.*
"Pyridine, 2,3-dibromo-5-(difluoromethyl)-6-methyl-", Database Registry [Online], Chemical Abstracts Service, Columbus, Ohio, U.S., XP002779415, Database accession No. 1805043-76-8, Sep. 11, 2015, 1 page.
"Pyridine, 3-bromo-2-chloro-5,6-dimethyl-", Database Registry [Online], Chemical Abstracts Service, Columbus, Ohio, U.S., XP002779416, Database accession No. 1780882-71-4, Jun. 15, 2015, 1 page.
"Pyridine, 3-bromo-2-chloro-5-(1-chloroethyl)-6-methyl", Database Registry [Online], Chemical Abstracts Service, Columbus, Ohio, U.S., XP002779411, Database accession No. 1823317-06-1, Dec. 6, 2015, 1 page.
"Pyridine, 3-bromo-2-chloro-5-(chloromethyl)-6-methyl", Database Registry [Online], Chemical Abstracts Service, Columbus, Ohio, U.S., XP002779410, Database accession No. 1824053-87-3, Dec. 7, 2015, 1 page.
"Pyridine, 3-bromo-2-chloro-5-(difluoromethyl)-6-methyl-", Database Registry [Online], Chemical Abstracts Service, Columbus, Ohio, U.S., XP002779412, Database accession No. 1806908-22-4, Sep. 14, 2015, 1 page.
"Pyridine, 3-bromo-2-fluoro-5,6-dimethyl-", Database Registry [Online], Chemical Abstracts Service, Columbus, Ohio, U.S., XP002779407, Database accession No. 2137579-23-6, Nov. 1, 2017, 1 page.
"Pyridine, 3-bromo-5-(bromomethyl)-2-chloro-6-methyl", Database Registry [Online], Chemical Abstracts Service, Columbus, Ohio, U.S., XP002779409, Database accession No. 1824266-59-6, Dec. 7, 2015, 1 page.
"Pyridine, 3-bromo-5-(difluoromethyl)-2-fluoro-6-methyl-", Database Registry [Online], Chemical Abstracts Service, Columbus, Ohio, U.S., XP002779413, Database accession No. 1806907-10-7, Sep. 14, 2015, 1 page.
"Pyridine, 3-bromo-5-(difluoromethyl)-2-iodo-6-methyl-", Database Registry [Online], Chemical Abstracts Service, Columbus, Ohio, U.S., XP002779414, Database accession No. 1805408-94-9, Sep. 11, 2015, 1 page.
"Pyridine, 5-bromo-2-methyl-3-(1,1,2,2,2-pentafuoroethyl)-", Database Registry [Online], Chemical Abstracts Service, Columbus, Ohio, U.S., XP002779428, Database accession No. 1346536-92-2, Nov. 29, 2011, 1 page.
"Pyridine, 5-bromo-2-methyl-3-(1-methylethyl)-", Database Registry [Online], Chemical Abstracts Service, Columbus, Ohio, U.S., XP002779431, Database accession No. 1346533-98-9, Nov. 29, 2011, 1 page.

(Continued)

*Primary Examiner* — Samantha L Shterengarts
(74) *Attorney, Agent, or Firm* — Marshall, Gerstein & Borun LLP

(57) ABSTRACT

The present invention relates to a process for the preparation pyridine derivatives of the formula (I).

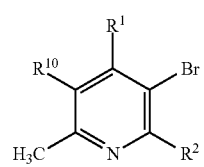

7 Claims, No Drawings

(56) References Cited

OTHER PUBLICATIONS

"Pyridine, 5-bromo-2-methyl-3-(2,2,2-trifluoroethyl)-", Database Registry [Online], Chemical Abstracts Service, Columbus, Ohio, U.S., XP002779426, Database accession No. 1346540-77-9, Nov. 29, 2011, 1 page.
"Pyridine, 5-bromo-2-methyl-3-(2-methylpropy1)-", Database Registry [Online], Chemical Abstracts Service, Columbus, Ohio, U.S., XP002779408, Database accession No. 2092465-24-0, Apr. 19, 2017, 1 page.
"Pyridine, 5-bromo-2-methyl-3-(trifluoromethyl)-", Database Registry [Online], Chemical Abstracts Service, Columbus, Ohio, U.S., XP002779437, Database accession No. 1211526-51-0, Mar. 18, 2010, 1 page.
"Pyridine, 5-bromo-3-(1,1-dulfuoroethyl)-2-methyl-", Database Registry [Online], Chemical Abstracts Service, Columbus, Ohio, U.S., XP002779429, Database accession No. 1346534-78-8, Nov. 29, 2011, 1 page.
"Pyridine, 5-bromo-3-(1-bromoethyl)-2-methyl-", Database Registry [Online], Chemical Abstracts Service, Columbus, Ohio, U.S., XP002779427, Database accession No. 1346539-17-0, Nov. 29, 2011, 1 page.
"Pyridine, 5-bromo-3-(1-chloroethyl)-2-methyl-", Database Registry [Online], Chemical Abstracts Service, Columbus, Ohio, U.S., XP002779432, Database accession No. 1346533-62-7, Nov. 29, 2011, 1 page.
"Pyridine, 5-bromo-3-(2,2-difluoroethyl)-2-methyl-", Database Registry [Online], Chemical Abstracts Service, Columbus, Ohio, U.S., XP002779430, Database accession No. 1346534-67-5, Nov. 29, 2011, 1 page.
"Pyridine, 5-bromo-3-(2-bormoethyl)-2-methyl-", Database Registry [Online], Chemical Abstracts Service, Columbus, Ohio, U.S., XP002779433, Database accession No. 1346533-58-1, Nov. 29, 2011, 1 page.
"Pyridine, 5-bromo-3-(2-chloroethyl)-2-methyl-", Database Registry [Online], Chemical Abstracts Service, Columbus, Ohio, U.S., XP002779425, Database accession No. 1346543-45-0, Nov. 29, 2011, 1 page.
"Pyridine, 5-bromo-3-(bromomethyl)-2-methyl-", Database Registry [Online], Chemical Abstracts Service, Columbus, Ohio, U.S., XP002779434, Database accession No. 1346533-53-6, Nov. 29, 2011, 1 page.
"Pyridine, 5-bromo-3-(fluoromethyl)-2-methyl-", Database Registry [Online], Chemical Abstracts Service, Columbus, Ohio, U.S., XP002779435, Database accession No. 1346531-70-1, Nov. 29, 2011, 1 page.
"Pyridine, 5-bromo-3-ethyl-2-methyl-", Database Registry [Online], Chemical Abstracts Service, Columbus, Ohio, U.S., XP002779436, Database accession No. 1346159-09-8, Nov. 22, 2011, 1 page.
Database Registry [Online], Chemical Abstracts Service, Columbus, Ohio, U.S., XP002779417, Database accession No. 1643577-42-7, Jan. 21, 2015, 1 page.
Database Registry [Online], Chemical Abstracts Service, Columbus, Ohio, U.S., XP002779418, Database accession No. 1643562-82-6, Jan. 21, 2015, 1 page.
Database Registry [Online], Chemical Abstracts Service, Columbus, Ohio, U.S., XP002779419, Database accession No. 1643543-77-4, Jan. 21, 2015, 1 page.
Database Registry [Online], Chemical Abstracts Service, Columbus, Ohio, U.S., XP002779420, Database accession No. 1643542-94-2, Jan. 21, 2015, 1 page.
Database Registry [Online], Chemical Abstracts Service, Columbus, Ohio, U.S., XP002779421, Database accession No. 1643538-58-2, Jan. 21, 2015, 1 page.
Database Registry [Online], Chemical Abstracts Service, Columbus, Ohio, U.S., XP002779422, Database accession No. 1643537-96-5, Jan. 21, 2015, 1 page.
Database Registry [Online], Chemical Abstracts Service, Columbus, Ohio, U.S., XP002779423, Database accession No. 1643537-80-7, Jan. 21, 2015, 1 page.
Database Registry [Online], Chemical Abstracts Service, Columbus, Ohio, U.S., XP002779424, Database accession No. 1643537-64-7, Jan. 21, 2015, 1 page.
Database Registry [Online], Chemical Abstracts Service, Columbus, Ohio, U.S., XP002779438, Database accession No. 118519-79-2, Sep. 17, 2009, 1 page.
Dunn, et al., "Bromination of Pyridines. II. Bromination of Aminopyridines", Journal Fur Praktische Chemie: Practical Applications and Applied Chemistry : Covering All Aspects of Applied Chemistry, vol. 331, Issue 3, 1989, pp. 369-374.
Dunn, et al., "The Bromination of Lutidines", Zeitschrift für Chemie, vol. 28, Issue 2, Feb. 1988, pp. 59-60.
European Search Report for EP Patent Application No. 18152984.3, dated Aug. 21, 2018, 16 pages.
International Patent Application No. PCT/EP2019/050794, International Search Report and Written Opinion, dated Apr. 16, 2019.
Mal, et al., "Conformational Control and Photoenolization of Pyridine-3-carboxaldehydes in the Solid State:? Stabilization of Photoenols via Hydrogen Bonding and Electronic Control", The Journal of Organic Chemistry, vol. 68, Issue 9, 2003, pp. 3446-3453.
Thalhammer, et al., "Inhibition of the histone demethylase JMJD2E by 3-substituted pyridine 2,4-dicarboxylates", Organic & Biomolecular Chemistry, vol. 9, Issue 1, 2011, pp. 127-135.

\* cited by examiner

BROMINATION OF PYRIDINE DERIVATIVES

CROSS-REFERENCE TO RELATED APPLICATIONS

This is the U.S. national phase of International Application No. PCT/EP2019/050794, filed Jan. 14, 2019, which claims the benefit of European Patent Application No. 18152984.3, filed on Jan. 23, 2018.

The present invention relates to a process for the preparation pyridine derivatives of the formula I

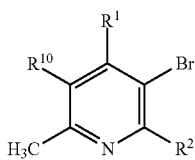

Bromination of similar pyridine derivatives is known from US 20140194386 and WO 2008/070740. One of the disadvantages of the reactions described in the above mentioned documents lies in the use of bromine in the presence of fuming sulfuric acid.

From Z. Chem 1988 28 2 50 a bromination is known using 65% oleum and $Br_2$. One of the disadvantages of the use of $Br_2$ as brominating agent is that the reaction is very slow and requires high temperatures. Furthermore, the use of $Br_2$ as brominating agent leads to a mixture of mono and dibromo isomers which are usually very difficult to purify.

Thus, it was an object of the present invention to overcome the disadvantages of the known processes and to provide an improved, selective and more economical and production plant friendly process.

It was now found that pyridine derivatives of the formula I

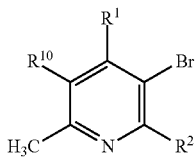

in which
$R^1$ is in each case independently selected from hydrogen, halogen, $C_1$-$C_6$-alkyl and $C_1$-$C_6$-halogenalkyl;
$R^2$ is in each case independently selected from hydrogen and halogen;
$R^{10}$ is in each case independently selected from H, halogen, $O(R^{95})$, $C_1$-$C_6$-alkyl and $C_1$-$C_6$-halogenalkyl; wherein
$R^{95}$ is $C_1$-$C_6$-alkyl, $C_1$-$C_6$-halogenalkyl;
can be obtained by reacting a compound of the formula II

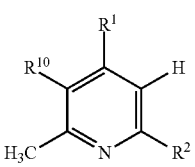

wherein $R^1$, $R^2$ and $R^{10}$ are as defined above with a brominating agent selected from the group consisting of such as N-bromosuccinimide (NBS), 1,3-dibromo-5,5-dimethylhydantoin (DBDMH) or a system consisting of $HBr/H_2O_2$ in the presence of oleum 65%.

The process of this invention is very selective because it leads to the desired pyridines with a low content of side products which is desirable from the economical point of view and such process is suitable for the production on a large scale.

Preferably the brominating agent in the process according to the invention is selected from the group consisting of such as N-bromosuccinimide (NBS), 1,3-dibromo-5,5-dimethylhydantoin (DBDMH) or a system consisting of $HBr/H_2O_2$. The preferred brominating agents are NBS and DBDMH. The most preferred brominating agent is 1,3-dibromo-5,5-dimethylhydantoin (DBDMH).

Typical reaction times are in the range of from 1 to 20 hours, preferably from 2 to 15 hours and more preferably from 3 to 10 hours, most preferably 3 to 5 hours.

Typical the product will be extracted using an inert organic solvent.

By "inert organic solvent" is meant an organic solvent which, under the reaction conditions of the process of this invention, does not enter into any appreciable reaction with either the reactants or the products.

In one embodiment, the inert organic solvent is selected from non-halogenated inert organic solvents; preferably from non-halogenated aliphatic hydrocarbons, non-halogenated cycloaliphatic hydrocarbons, non-halogenated aromatic hydrocarbons, halogenated aliphatic hydrocarbons, halogenated aromatic hydrocarbons, ethers, esters, ketones, and any combination thereof.

Examples of suitable non-halogenated aliphatic hydrocarbons include pentane, hexane, heptane, and the like. Preference is given to saturated aliphatic hydrocarbons having from 5 to 10 carbon atoms.

Examples of suitable non-halogenated cycloaliphatic hydrocarbons include cyclopentane, cyclohexane, cycloheptane, and the like. Preference is given to non-halogenated saturated cycloaliphatic hydrocarbons having from 5 to 10 carbon atoms. Cyclohexane is particularly preferred.

Examples of suitable a non-halogenated aromatic hydrocarbons include toluene, o-xylene, m-xylene, p-xylene, ethylbenzene, 2-propylbenzene (cumene), 2-isopropyltoluene (o-cymol), 3-isopropyltoluene (m-cymol), 4-isopropyltoluene (p-cymol), 1,3,5-trimethylbenzene (mesitylene), and the like. Preference is given to toluene, o-xylene, m-xylene, p-xylene, ethylbenzene, 1,3,5-trimethylbenzene (mesitylene), and any combination thereof. Especially preferred among the non-halogenated aromatic hydrocarbons are toluene, o-xylene, m-xylene, p-xylene, and any combination thereof, with toluene being the most preferred.

Examples of suitable halogenated aliphatic hydrocarbons include dichloromethane, chloroform, carbon tetrachloride, 1,2-dichloroethane, 1,1,1,2-tetrachloroethane, 1,1,2,2-tetrachloroethane, 1,1-dichloroethylene, 1,2-dichloroethylene, and the like. Preference is given to dichloromethane and 1,2-dichloroethane and any combination thereof.

Examples of suitable halogenated aromatic hydrocarbons include chlorobenzene, bromobenzene, o-dichlorobenzene, m-dichlorobenzene, α,α,α-trifluorotoluene (benzotrifluoride) and the like and any combination thereof.

Examples of suitable ethers include cyclic and acyclic ethers such as diethyl ether, diisopropyl ether, n-butyl methyl ether, isobutyl methyl ether, sec-butyl methyl ether, tert-butyl methyl ether, cyclopentyl methyl ether, methyltetrahydrofuran, tetrahydrofuran, 1,4-dioxane, and the like and any combination thereof.

Examples of suitable esters include ethyl acetate, n-propylacetate, isopropyl acetate, n-butyl acetate, tert-butyl acetate, and the like and any combination thereof.

Examples of suitable ketones include acetone, methyl ethyl ketone, methyl isopropyl ketone, methyl isobutyl ketone, cyclopropyl methyl ketone and the like, and any combination thereof.

After the extraction the inert solvent will be evaporated and the crude product will be purified by distillation.

The molar ratio of the brominating agent DBDMH to the pyridine derivative of the formula I where $R^1$=H and $R^2$=H can vary widely and depends on the reaction conditions used, but is generally from 0.40:1.1 to 1.5:1, preferably from 0.40:1 to 1.2:1, more preferably from 0.40:1 to 1.1:1 and even more preferably from 0.50:1 to 1.0:1. It is preferably to use the brominating agent less then 1 eq compared to the pyridine in order to avoid sideproducts. Therefore, the molar ratio of the brominating agent DBDMH to the pyridine derivative of the formula I where $R^1$=H and $R^2$=H is preferably 0.4 to 1.1, more preferably 0.4 to 0.9.

Preferably, a bromination of the compounds of the formula I where $R^1$=H and $R^2$=H will be performed. The preferred brominating agent is 1,3-dibromo-5,5-dimethylhydantoin (DBDMH). In that case, preference is given to performing the bromination without an additional solvent.

In this case, the the reaction temperature is preferably in the range from 0 to 150° C. and especially 80 to 125° C. temperature and the reaction times are in the range of from 2 to 10 hours, more preferred 2 to 5 hours.

Preferably the purification is a distillation under reduced pressure (50-55° C.; 1.6-2.0 mbar).

The brominated pyridine obtained according to the inventive process (step (i)) can be further converted into 2,3-disubstituted pyridine compounds of the formula III

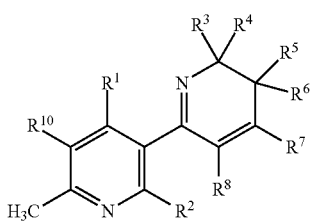

wherein
$R^1$ is in each case independently selected from hydrogen, halogen, $C_1$-$C_6$-alkyl and $C_{1-6}$-halogenalkyl;
$R^2$ is in each case independently selected from hydrogen and halogen;
$R^3$, $R^4$ are independently selected from $C_1$-$C_6$-alkyl, $C_2$-$C_6$-alkenyl, $C_2$-$C_6$-alkynyl, $C_1$-$C_6$-halogenalkyl, $C_2$-$C_6$-halogenalkenyl and $C_2$-$C_6$-halogenalkynyl;
$R^5$ is halogen;
$R^6$ is halogen;
$R^7$, $R^8$ together with the carbon atoms to which they are bound form a ring A, wherein the ring A is phenyl and wherein the ring A is substituent by $(R^{78})_o$, wherein o is 0, 1, 2 or 3; and
$R^{78}$ is independently selected from halogen, $C_1$-$C_6$-alkyl, $C_1$-$C_6$-alkoxy, $C_1$-$C_6$-halogenalkyl and $C_1$-$C_6$-halogenalkoxy;

$R^{10}$ is in each case independently selected from H, halogen, $O(R^{95})$, $C_1$-$C_6$-alkyl and $C_1$-$C_6$-halogenalkyl; wherein $R^{95}$ is $C_1$-$C_6$-alkyl, $C_1$-$C_6$-halogenalkyl.

Consequently, the present invention relates further to the process comprises the following step:
(i) providing a compound of the formula I as described above;
(ii) reacting the compound of the formula I with a compound of the formula IV

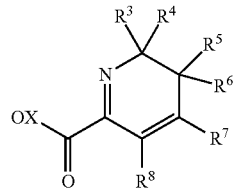

in which
$R^3$, $R^4$, $R^5$, $R^6$, $R^7$ and $R^8$ are each as defined for formula III; and X is a metal ion.

The step (ii) in carried out in the presence of a catalyst.

According to one embodiment of the invention the catalyst comprises: a Cu source, a Pd source and an optional ligand.

When carrying out the reaction, the catalyst system (Pd+ligand) can be added together or separately either at room temperature or at an elevated temperature. The system can be prepared separately, immediately before the reaction is carried out, by combining a Pd salt and the ligand, or it can be synthesized before or purchased in pure form or in solution. Also possible is the direct addition of the ligand and of the palladium source to the batch (in situ process). Alternatively the reaction can be carried out with a palladium source alone without addition of an additional ligand.

The palladium catalysts used are optionally produced in situ from at least one palladium(II) salt or a palladium(0) compound and the corresponding phosphine ligands. However, they may also be used directly as palladium(0)- or palladium(II)-compound without reducing the initial catalytic activity.

According to one embodiment of the invention the Pd source is selected from the group consisting of $Pd(OAc)_2$, $Pd(II)Cl_2$, Palladium(II)-1,2-bis(diphenylphosphino)ethan dichloride, Palladium(II)-1,3-Bis(diphenylphosphino)propan dichloride, Palladium(II)-1,4-Bis(diphenylphosphino) butan dichloride, Palladium(II)-1,1'-Bis(diphenylphosphino)ferrocene dichloride, Palladium(0)-tetrakis (triphenylphosphin, Palladium(II)bis(triphenylphosphin) dichloride, $Pd(P(t-Bu)_3)_2$, $Pd(acac)_2$, $Pd(iPr)_2Ph_2$, $Pd(P(t-Bu)_2Ph)_2Cl_2$, $Pd(dba)_2$, $PdI_2$, $PdBr_2$, or $Pd(TFA)_2$.

According to one embodiment of the invention the ligand is mono- or bidentate phosphorus-containing ligand.

As monodentate phosphorus-containing ligand following are preferred:
monodentate phosphorus-containing ligand of the formula P

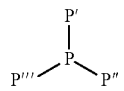

wherein

P', P", P''' are independently selected from $C_1$-$C_6$-alkyl, $C_3$-$C_6$-cycloalkyl, aryl and heteroaryl, which are unsubstituted or substituted.

More preferred are monodentate phosphorus-containing ligand selected from the group consisting of: triethylphosphin, tri-n-butylphosphin, tri-t-butylphosphin, tribenzylphosphin, tri(cyclopentyl)phosphin, tri(cyclohexyl)phosphin, triphenylphosphin, tri(p-tolyl)phosphin, tri(mtolyl)phosphin, tri (o-tolyl)phosphin, tri(p-methoxyphenyl)phosphin, tri(p-dimethylaminophenyl)phosphin, tri-(natrium-meta-sulfonatophenyl)-phosphan, diphenyl(2-sulfonatophenyl)phosphin, tri(1-naphthyl)phosphin, di-t-butyl-phenyl-phosphin, XPhos, SPhos, RuPhos und diphenyl-2-pyridylphosphin. Most preferred are triphenylphosphin, tri(p-tolyl)phosphin und tri(cyclohexyl)phosphin.

As bidentate phosphorus-containing ligand following are preferred: 2,2'-Bis(diphenylphosphino)-1,1'-binaphthyl (BINAP), 1,1-bis(diphenylphosphino)methane (DPPM), 1,2-bis(diphenylphosphino)ethan (DPPE), 1,3-bis(diphenylphosphino)propan (DPPP), 1,4-bis(diphenylphosphino)butan (DPPB), 1,1'-bis(diphenylphosphino)ferrocen (DPPF), 4,5-bis(diphenylphosphino)-9,9-dimethylxanthen (Xantphos), 1,2-bis(di-tertbutylphosphinomethyl)benzol, 1,2-bis(di-tert-pentylphosphinomethyl)benzol), 1,3-bis(diphenylphosphino)-2,2-dimethylpropane, 1,3-bis(diphenylphosphino)-2-methyl-2-butylpropane und 1,2-bis(di-tert-butylphosphinomethyl)naphthalin. Most preferred are 1,2-bis(diphenylphosphino)ethan (DPPE), 1,3-bis(diphenylphosphino)propan (DPPP), 1,4-bis(diphenylphosphino)butan (DPPB and 1,1'-bis(diphenylphosphino)ferrocen (DPPF).

The molar ratio of palladium to the phosphine ligand should be between 4:1 and 1:100 and is preferably between 1:1 and 1:5, particularly preferably between 1:1 and 1:2.

When carrying out the reaction, the catalyst system (Pd+ ligand) can be added together or separately either at room temperature or at an elevated temperature. The system can be prepared separately, immediately before the reaction is carried out, by combining a Pd salt and the ligand, or it can be purchased or synthesized in pure form or in solution. Also possible is the direct addition of the ligand and of the palladium source to the batch (in situ process).

According to one embodiment of the invention the Cu salts is selected from the group CuI, CuBr, CuCl, CuF, $Cu_2O$, Cu(OAc), $Cu_2(CO_3)(OH)_2$, $CuSO_4$, CuO, Cu(Otriflate)$_2$, Cu(OAc)$_2$. Most preferred are CuBr, CuCl, $Cu_2O$, $CuSO_4$ and CuO.

The molar ratio of palladium to Cu salt should be between 0.01 and 50, preferably between 0.05 and 20, preferred between 0.1 and 5.

Suitable organic solvents for the reaction are aprotic solvents, for example aromatic hydrocarbons such as benzene, toluene, xylenes, cumene, chlorobenzene, dichlorobenzenes, nitrobenzene or tert-butylbenzene, aprotic polar solvents, for example cyclic or acyclic ethers such as diethyl ether, diisopropyl ether, tert-butyl methyl ether (MTBE), tert-butyl ethyl ether, tetrahydrofuran (THF) or dioxane, cyclic or acyclic amides such as dimethylformamide, dimethylacetamide, N-methylpyrrolidone or tetramethylurea, aliphatic esters like ethyl acetate, butyl acetate or methyl propionate, cyclic or acyclic ketones like cyclohexanone, acetone, 3-methyl-butanone or 4-methyl-pentanone-2, aliphatic chlorinated solvents like dichloromethane, chloroform, tetrachloromethane, 1,2-dichloroethane, 1,1,2-trichloroethylene or aliphatic nitriles such as acetonitrile or propionitrile, and mixtures of the aforementioned solvents. The preference is given to acetonitrile, 3-methylbutanone, 4-methyl-pentanone-2, ethyl acetate, butyl acetate, N-methylpyrrolidone, dimethylformamide, toluene, xylenes, even more preferred toluene, N-methylpyrrolidone or butyl acetate.

The reaction usually takes place at temperatures between 50° C. and 200° C., preferred between 70° C. and 150° C., especially preferred between 90° C. and 130° C.

In the compound of the formula IV X is selected form the group consisting of Li, Na, K and Cs. Most preferred is Li.

The compound of the formula IV can be prepared from the compound of the formula V

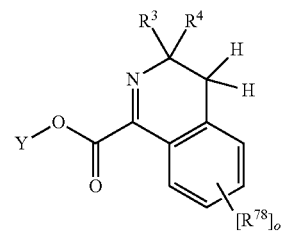

I wherein $R^3$, $R^4$ are independently selected from $C_1$-$C_6$-alkyl, $C_2$-$C_6$-alkenyl, $C_2$-$C_6$-alkynyl, $C_1$-$C_6$-halogenalkyl, $C_2$-$C_6$-halogenalkenyl and $C_2$-$C_6$-halogenalkynyl;

$R^{78}$ is independently selected from halogen, $C_1$-$C_6$-alkyl, $C_1$-$C_6$-alkoxy, $C_1$-$C_6$-halogenalkyl and $C_1$-$C_6$-halogenalkoxy;

o is 0, 1, 2 or 3;

Y is selected from $C_1$-$C_6$-alkyl, $C_1$-$C_6$-halogenalkyl, phenyl and benzyl, wherein phenyl and benzyl are unsubstituted or substituted by CN, $NO_2$, halogen, $C_1$-$C_6$-alkyl, $C_1$-$C_6$-halogenalkyl or $C_1$-$C_6$-alkoxy.

which can be obtained by one step reaction of the compound of the formula VI

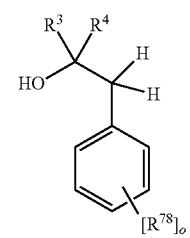

VI wherein $R^3$, $R^4$, o and $R^{78}$ are as defined above with a compound of the formula VII

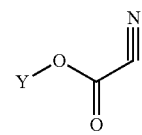

VII wherein Y is as defined above.

According to one embodiment of the invention the reaction is carried out in the presence of an acid.

Preferably the acid is selected from inorganic acids such as sulfuric acid, fuming sulfuric acid, nitric acid, phosphoric acid, hydrobromic acid, hydrochloric acid, hydrofluoric acid, organic acids such as trifluoromethane sulfonic acid, methane sulfonic acid, trifluoro acetic acid, trichloro acetic acid and mixtures thereof.

More preferred as acid are sulfuric acid, fuming sulfuric acid and trifluoro acetic acid.

Most preferred is the use of sulfuric acid. Preferred amounts of the acid used are 1-10 equivilants related to the alcohol VI used, more preferred 2 to 8 equivilants, even more preferred 2.5 to 5 equivilants.

According to embodiment of the invention the reaction between VI and VII is carried out in an inert solvent.

By "inert organic solvent" is meant an organic solvent which, under the reaction conditions of the process of this invention, does not enter into any appreciable reaction with either the reactants or the products.

In one embodiment, the inert organic solvent is selected from non-halogenated inert organic solvents; preferably from non-halogenated aliphatic hydrocarbons, non-halogenated cycloaliphatic hydrocarbons, non-halogenated aromatic hydrocarbons, halogenated aliphatic hydrocarbons, halogenated aromatic hydrocarbons, amides, ethers, esters, ketones, nitriles and any combination thereof.

Examples of suitable non-halogenated aliphatic hydrocarbons include pentane, hexane, heptane, petrolether and the like. Preference is given to saturated aliphatic hydrocarbons having from 5 to 10 carbon atoms.

Examples of suitable non-halogenated cycloaliphatic hydrocarbons include cyclopentane, cyclohexane, cycloheptane, and the like. Preference is given to non-halogenated saturated cycloaliphatic hydrocarbons having from 5 to 10 carbon atoms. Cyclohexane is particularly preferred.

Examples of suitable a non-halogenated aromatic hydrocarbons include toluene, o-xylene, m-xylene, p-xylene, ethyl benzene, 2-propylbenzene (cumene), 2-isopropyltoluene (o-cymol), 3-isopropyltoluene (m-cymol), 4-isopropyltoluene (p-cymol), 1,3,5-trimethylbenzene (mesitylene), and the like. Preference is given to toluene, o-xylene, m-xylene, p-xylene, ethylbenzene, 1,3,5-trimethylbenzene (mesitylene), and any combination thereof. Especially preferred among the non-halogenated aromatic hydrocarbons are toluene, o-xylene, m-xylene, p-xylene, and any combination thereof, with toluene being the most preferred.

Examples of suitable halogenated aliphatic hydrocarbons include dichloromethane, chloroform, carbon tetrachloride, 1,2-dichloroethane, 1,1,1,2-tetrachloroethane, 1,1,2,2-tetrachloroethane, 1,1-dichloroethylene, 1,2-dichloroethylene, and the like. Preference is given to dichloromethane and 1,2-dichloroethane and any combination thereof.

Examples of suitable halogenated aromatic hydrocarbons include chlorobenzene, bromobenzene, o-dichlorobenzene, m-dichlorobenzene, α,α,α-trifluorotoluene (benzotrifluoride) and the like and any combination thereof.

Examples of suitable amides include N,N-dimethylformamide, N,N-dimethylacetamide, N,N-diethylacetamide, N-methyl-pyrrolidone, and the like and any combination thereof.

Examples of suitable ethers include cyclic and acyclic ethers such as diethyl ether, diisopropyl ether, n-butyl methyl ether, isobutyl methyl ether, sec-butyl methyl ether, tert-butyl methyl ether, cyclopentyl methyl ether, tetrahydrofuran, 1,4-dioxane, and the like and any combination thereof.

Examples of suitable esters include ethyl acetate, n-propylacetate, isopropyl acetate, tert-butyl acetate, and the like and any combination thereof.

Examples of suitable ketones include acetone, methyl ethyl ketone, methyl isopropyl ketone, methyl isobutyl ketone, cyclopropyl methyl ketone and the like, and any combination thereof.

Examples of suitable nitriles include acetonitrile, benzonitrile, and the like and any combination thereof.

Preferably the inert solvent selected from the group consisting of aliphatic and aromatic hydrocarbons and halohydrocarbons such as cyclohexane, heptane, benzene, toluene, xylenes, cumene, mesitylene, chlorobenzene, dichlorobenzenes and tert-butylbenzene, cyclic or acyclic ethers such as diethyl ether, diisopropyl ether, tert-butyl methyl ether (MTBE), tert-butyl ethyl ether, methyl cyclopentylether, tetrahydrofuran (THF), methyl tetrahydrofuran (methyl THF) or dioxane, nitriles such as acetonitrile and propionitrile, aliphatic halohydrocarbons such as dichloromethane, dichloroethane, trichloromethane and mixtures thereof.

More preferably the inert solvent is chlorobenzene, cyclohexane, heptane or petrolether.

Compounds VII are commercially available or can be synthesized according to known procedures. For details see: Heteroatom Chemistry, 26(4), 249-256; 2015; CH 675875; Anorganische and Allgemeine Chemie, 510, 136-42; 1984; Tetrahedron Letters, (27), 2517-20; 1979; Journal of Organic Chemistry, 41(21), 3486-7; 1976; Bioorganic & Medicinal Chemistry, 23(24), 7661-7670; 2015; DE 102014008070; WO 2017059191; Tetrahedron, 63(39), 9724-9740; 2007; Chemical Communications, (16), 1775-1777; 2006; Organic & Biomolecular Chemistry, 2(13), 1921-1933; 2004; Tetrahedron Letters, (27), 2517-20; 1979.

Compounds VI are commercially available or can be synthesized according to known procedures. For details see: Tetrahedron, 42(11), 2931-5; 1986; Journal of the Indian Chemical Society, 87(5), 595-600; 2010; Chemistry Letters, 37(7), 800-801; 2008; Journal of Labelled Compounds & Radiopharmaceuticals, 43(14), 1321-1326; 2000; Organic Chemistry, 47(7), 1193-6; 1982; Chemische Berichte, 114 (12), 3813-30; 1981; Russian Chemical Bulletin, 55(1), 123-136; 2006; Comptes Rendus des Seances de l'Academie des Sciences, Serie C: Sciences Chimiques, 283(3), 75-8; 1976; Journal of Organometallic Chemistry, 328(1-2), 81-6; 1987; WO 2016038628; WO 2008090193; Chemistry Letters, 37(7), 800-801; 2008; European Journal of Medicinal Chemistry, 14(2), 165-70; 1979; Journal of Organic Chemistry, 45(19), 3925-7; 1980; Chemical Communications, 51(30), 6637-6639; 2015; Journal of the American Chemical Society, 110(23), 7737-45; 1988; Tetrahedron Letters, 50(20), 2320-2321; 2009; Journal of Medicinal Chemistry, 14(2), 165-70; 1979; Angewandte Chemie, International Edition, 53(25), 6439-6442; 2014; Bulletin de la Societe Chimique de France, (5), 787-93; 1985; Chemical Communications, 52(82), 12147-12150; 2016; European Journal of Medicinal Chemistry, 14(2), 165-70; 1979.

Preferably, the compound VI is used in an amount of 0.8 eq to 3 eq, in particular 1.05 to 2.5 eq, more specifically 1.05 to 1.8 eq, in relation to one equivalent of compound VII.

The substituted dihydroisoquinolines of the formula V obtained according to the inventive process can be further converted into compounds of the formula VIII

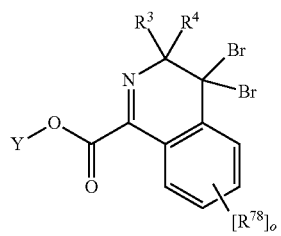

VIII wherein
$R^3$, $R^4$ are independently selected from $C_1$-$C_6$-alkyl, $C_2$-$C_6$-alkenyl, $C_2$-$C_6$-alkynyl, $C_1$-$C_6$-halogenalkyl, $C_2$-$C_6$-halogenalkenyl and $C_2$-$C_6$-halogenalkynyl;
$R^{78}$ is independently selected from halogen, $C_1$-$C_6$-alkyl, $C_1$-$C_6$-alkoxy, $C_1$-$C_6$-halogenalkyl and $C_1$-$C_6$-halogenalkoxy;
o is 0, 1, 2 or 3;
Y is selected from $C_1$-$C_6$-alkyl, $C_1$-$C_6$-halogenalkyl, phenyl and benzyl, wherein phenyl and benzyl are unsubstituted or substituted by CN, $NO_2$, halogen, $C_1$-$C_6$-alkyl, $C_1$-$C_6$-halogenalkyl or $C_1$-$C_6$-alkoxy.

Consequently, the present invention relates further to the process comprises the following step:
(i) providing a compound of the formula V
(ii) reacting the compound of the formula V with a brominating agent.

According to one embodiment of the invention the brominating agent in the process according to the invention is selected from the group consisting of is selected from the group consisting of $Br_2$, N-bromosuccinimide (NBS), 1,3-dibromo-5,5-dimethylhydantoin (DBDMH) or a system consisting of $HBr/H_2O_2$.

Preferably the brominating agent is N-bromosuccinimide (NBS).

Preferably the brominating agent is 1,3-dibromo-5,5-dimethylhydantoin (DBDMH).

Preferably, the brominating agent is used in an amount of 1.5 eq to 5 eq, in particular 2.0 to 3.0 eq, in relation to one equivalent of compound V.

Typical reaction times are in the range of from 10 minutes to 12 hours, preferably from 30 minutes to 8 hours, also preferred from 1 to 4 hours.

Typically the bromination is carried out under radical generating conditions. Preferred radical generating conditions are the use of UV-light or the use of radical initiators like azo compounds or peroxides. Preferred conditions are the use of radical initiators. The nature of the radical initor depends on the reaction temperatures applied, most preferred are benzoyl peroxide or AIBN (azo isobutyro dinitrile). The amounts of radical initiators used range from 0.001 equiv. to 0.5 equiv., preferably 0.005 eqiv. to 0.3 equiv., also preferred 0.01 to 0.2 equiv. related to compound V used.

Typically the reaction is carried out in an inert solvent as defined above. Preferred inert solvents for this bromination step are chlorobenzene, cyclohexane, heptane, trichloromethane, tetrachloromethane, ethyl acetate, butyl acetate or acetonitrile. Preferably the solvent used is chlorobenzene, cyclohexane, ethyl acetate or butyl acetate.

By means of the inventive process, the pyridine derivatives of the formula I can be prepared in high yields. Preferably, the yields are at least 60%, more preferably 70%, even more preferred at least 75%, even more preferred at least 80%.

The brominated dihydroisoquinolines of the formula VIII obtained according to the inventive process can be further converted into compounds of the formula IX

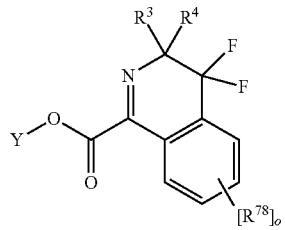

IX wherein
$R^3$, $R^4$ are independently selected from $C_1$-$C_6$-alkyl, $C_2$-$C_6$-alkenyl, $C_2$-$C_6$-alkynyl, $C_1$-$C_6$-halogenalkyl, $C_2$-$C_6$-halogenalkenyl and $C_2$-$C_6$-halogenalkynyl;
$R^{78}$ is independently selected from halogen, $C_1$-$C_6$-alkyl, $C_1$-$C_6$-alkoxy, $C_1$-$C_6$-halogenalkyl and $C_1$-$C_6$-halogenalkoxy;
o is 0, 1, 2 or 3;
Y is selected from $C_1$-$C_6$-alkyl, $C_1$-$C_6$-halogenalkyl, phenyl and benzyl, wherein phenyl and benzyl are unsubstituted or substituted by CN, $NO_2$, halogen, $C_1$-$C_6$-alkyl, $C_1$-$C_6$-halogenalkyl or $C_1$-$C_6$-alkoxy.

Consequently, the present invention relates further to the process comprises the following step:
(i) providing a compound of the formula V;
(ii) providing a compound of the formula VIII;
(iii) reacting the compound of the formula VIII with a fluorinating agent to provide the compound of the formula IX.

According to the one further embodiment of the invention the fluorinating agent is selected from the group consisting of NaF, CsF, KF, $KHF_2$, Olah reagent, HF, a polyhydrofluoride complex of a trialkylamine or mixtures of HF in trialkylamines $(C_1$-$C_6$-alkyl$)_3$N.

Polyhydrofluoride complex of a trialkylamine can be described by a formula $(C_1$-$C_6$-alkyl$)_3$N×n HF, wherein (n=1-5) such as: $(C_2H_5)_3$N×3 HF, $(C_4H_9)_3$N×3 HF.

Mixtures of HF in trialkylamines $(C_1$-$C_6$-alkyl$)_3$N are mixture with a content of 5-95% HF in trialkylamines $(C_1$-$C_6$-alkyl$)_3$N, preferred 10-60% HF, further preferred 20-40%.

Preferably the fluorinating agent is HF in triethylamine solution, preferred $(C_2H_5)_3$N×3 HF, optionally diluted with $(C_2H_5)_3$N or with mixtures of $(C_2H_5)_3$N and polar solvents like acetonnitril, dimethylformamide or N-methyl-pyrrolidone.

Preferably, the fluorinating agent is used in an amount of 1.2 eq to 10 eq, in particular 2.2 to 7.8 eq, more specifically 4.4 to 5.6 eq, in relation to one equivalent of compound VIII.

According to the one further embodiment of the invention the fluorinating reaction is carried out in the presence of a solvent, preferably a polar solvent Suitable organic solvents for the reaction are protic polar solvents, for example water, aliphatic alcohols having preferably from 1 to 4 carbon atoms, such as methanol, ethanol, n-propanol, isopropanol, n-butanol, isobutanol or tertbutanol, or carboxylic acids such as acetic acid, aromatic hydrocarbons such as benzene, toluene, xylenes, cumene, chlorobenzene, nitrobenzene or tert-butylbenzene, aprotic polar solvents, for example cyclic or acyclic ethers such as diethyl ether, diisopropyl ether, tert-butyl methyl ether (MTBE), tert-butyl ethyl ether, tetrahydrofuran (THF) or dioxane, cyclic or acyclic amides such as dimethylformamide, dimethylacetamide, N-methylpyrrolidone or tetramethylurea, aliphatic esters like ethyl acetate, butyl acetate or methyl propionate, cyclic or acyclic ketones like cyclohexanone, acetone, 3-methyl-butanone or 4-methyl-pentanone-2, aliphatic tertiary amines like triethylamine, tributylamine or diisopropyl ethylamine, or aliphatic nitriles such as acetonitrile or propionitrile, and mixtures of the aforementioned solvents. The preference is given to water, acetonitrile, 3-methylbutanone, butyl acetate, dimethylformamide, ethanol, toluene.

Preferably the polar solvent is acetonitril or triethylamine.

Further preferred solvent systems are $(C_2H_5)_3N \times 3$ HF alone or $(C_2H_5)_3N \times 3$ HF with addition of triethylamine, acetonitrile or dimethylformamide.

The reaction usually takes place at temperatures between 10° C. and 150° C., preferred between 20° C. and 100° C., especially preferred between 50° C. and 90° C.

Typical reaction times are in the range of from 0.5 to 18 hours, preferred 1 to 5 hours, preferably from 1 to 3 hours.

The terms "compounds I", "compounds II", "compounds IIa" and "compounds III" refer to compounds of formulae I, II, IIa and III, respectively. In the definitions of the variables given above, collective terms are used which are generally representative for the substituents in question.

In the definitions of the variables given herein, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_1$-$C_6$-halogenalkyl" refers to an alkyl group having 1 or 6 carbon atoms as defined above, wherein some or all of the hydrogen atoms in these groups may be replaced by halogen atoms as mentioned above. Examples are "$C_1$-$C_2$-haloalkyl" groups such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_2$-$C_6$-alkenyl" refers to a straight-chain or branched unsaturated hydrocarbon radical having 2 to 6 carbon atoms and a double bond in any position. Examples are "$C_2$-$C_4$-alkenyl" groups, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-halogenalkenyl" refers to an alkyl group having 2 or 6 carbon atoms as defined above, wherein some or all of the hydrogen atoms in these groups may be replaced by halogen atoms as mentioned above.

The term "$C_2$-$C_6$-alkynyl" refers to a straight-chain or branched unsaturated hydrocarbon radical having 2 to 6 carbon atoms and containing at least one triple bond. Examples are "$C_2$-$C_4$-alkynyl" groups, such as ethynyl, prop-1-ynyl, prop-2-ynyl (propargyl), but-1-ynyl, but-2-ynyl, but-3-ynyl, 1-methyl-prop-2-ynyl.

The term "$C_2$-$C_6$-halogenalkynyl" refers to an alkyl group having 2 or 6 carbon atoms as defined above, wherein some or all of the hydrogen atoms in these groups may be replaced by halogen atoms as mentioned above.

The term "$C_1$-$C_6$-alkoxy" refers to a straight-chain or branched alkyl group having 1 to 6 carbon atoms which is bonded via an oxygen, at any position in the alkyl group. Examples are "$C_1$-$C_4$-alkoxy" groups, such as methoxy, ethoxy, n-propoxy, 1-methylethoxy, butoxy, 1-methyl-propoxy, 2-methylpropoxy or 1,1-dimethylethoxy.

The term "$C_1$-$C_6$-halogenalkoxy" refers to a $C_1$-$C_6$-alkoxy radical as defined above, wherein some or all of the hydrogen atoms in these groups may be replaced by halogen atoms as mentioned above. Examples are "$C_1$-$C_4$-haloalkoxy" groups, such as $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro-ethoxy, $OC_2F_5$, 2-fluoropropoxy, 3-fluoropropoxy, 2,2-difluoropropoxy, 2,3-difluoro-propoxy, 2 chloropropoxy, 3-chloropropoxy, 2,3-dichloropropoxy, 2-bromo--propoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bromomethyl-2-bromo--ethoxy, 4-fluorobutoxy, 4-chlorobutoxy, 4-bromobutoxy or non-afluorobutoxy.

The term "phenyl-$C_1$-$C_6$-alkyl" refers to alkyl having 1 to 6 carbon atoms (as defined above), wherein one hydrogen atom of the alkyl radical is replaced by a phenyl radical. Likewise, the terms "phenyl-$C_2$-$C_6$-alkenyl" and "phenyl-$C_2$-$C_6$-alkynyl" refer to alkenyl and alkynyl, respectively, wherein one hydrogen atom of the aforementioned radicals is replaced by a phenyl radical.

The meanings and preferred meanings described in the following for the variables $R^1$, $R^2$, $R^3$, $R^4$, $R^5$, $R^6$, $R^7$, $R^{78}$, $R^{95}$, $R^{10}$ and o apply to compounds and the compounds of the formula I, II, III and IV and side products in any of the above detailed inventive processes.

According to one embodiment of the invention in compounds of the formula I and, where applicable, II, III and IV the variables have independently of each other or more preferably in combination the following meanings:

$R^1$ is in each case independently selected from hydrogen and $C_1$-$C_6$-alkyl;

$R^2$ is in each case independently selected from hydrogen;

$R^3$, $R^4$ are independently selected from $C_1$-$C_6$-alkyl and $C_1$-$C_6$-halogenalkyl;

$R^5$ is halogen;

$R^6$ is halogen;

R⁷, R⁸ together with the carbon atoms to which they are bound form a ring A, wherein the ring A is phenyl and wherein the ring A is substituent by $(R^{78})_o$, wherein
o is 0, 1, 2 or 3; and
$R^{78}$ are independently selected from halogen and $C_1$-$C_6$-alkyl;
$R_{10}$ is independently selected from from $C_1$-$C_6$-alkyl, $C_1$-$C_6$-Alkox, and $C_1$-$C_6$-halogenalkyl.

According to one further embodiment of the invention in compounds of the formula I and, where applicable, II, III and IV the variables have independently of each other or more preferably in combination the following meanings:
$R^1$ is hydrogen;
$R^2$ is hydrogen;
$R^3$, $R^4$ are independently selected from $C_1$-$C_6$-alkyl and $C_1$-$C_6$-halogenalkyl;
$R^5$ is halogen;
$R^6$ is halogen;
R⁷, R⁸ together with the carbon atoms to which they are bound form a ring A, wherein the ring A is phenyl and wherein the ring A is substituent by $(R^{78})_o$, wherein
o is 0, 1, 2 or 3; and
$R^{78}$ are independently selected from halogen and $C_1$-$C_6$-alkyl;
$R_{10}$ is independently selected from from $C_1$-$C_6$-alkyl and $C_1$-$C_6$-halogenalkyl.

According to one further embodiment of the invention in compounds of the formula I and, where applicable, II, III and IV the variables have independently of each other or more preferably in combination the following meanings:
$R^1$ is hydrogen;
$R^2$ is hydrogen;
$R^3$, $R^4$ are independently $C_1$-$C_6$-alkyl;
$R^5$ is halogen;
$R^6$ is halogen;
R⁷, R⁸ together with the carbon atoms to which they are bound form a ring A, wherein the ring A is phenyl and wherein the ring A is substituent by $(R^{78})_o$, wherein
o is 0, 1, 2 or 3; and
$R^{78}$ are independently selected from halogen and $C_1$-$C_6$-alkyl;
$R_{10}$ are independently selected from $C_1$-$C_6$-alkyl and $C_1$-$C_6$-halogenalkyl.

According to one further embodiment of the invention in compounds of the formula I and, where applicable, II, III and IV the variables have independently of each other or more preferably in combination the following meanings:
$R^1$ is hydrogen;
$R^2$ is hydrogen;
$R^3$, $R^4$ are independently $C_1$-$C_6$-alkyl;
$R^5$ is F;
$R^6$ is F;
R⁷, R⁸ together with the carbon atoms to which they are bound form a ring A, wherein the ring A is phenyl and wherein the ring A is substituent by $(R^{78})_o$, wherein
o is 0, 1, 2 or 3; and
$R^{78}$ are independently selected from halogen and $C_1$-$C_6$-alkyl;
$R^{10}$ is independently selected from $C_1$-$C_6$-alkyl and $C_1$-$C_6$-halogenalkyl.

According to one further embodiment of the invention in compounds of the formula I and, where applicable, II, III and IV the variables have independently of each other or more preferably in combination the following meanings:
$R^1$ is hydrogen;
$R^2$ is hydrogen;
$R^3$, $R^4$ are independently $C_1$-$C_6$-alkyl;
$R^5$ is F;
$R^6$ is F;
R⁷, R⁸ together with the carbon atoms to which they are bound form a ring A, wherein the ring A is phenyl and wherein the ring A is substituent by $(R^{78})_o$, wherein
o is 0, 1, 2 or 3; and
$R^{78}$ are independently selected from halogen and $C_1$-$C_6$-alkyl;
$R^{10}$ is independently selected from $CH_3$ and $CHF_2$.

Particularly preferred active compounds I are selected from the group consisting of compounds I.A to IZA:
I.A: 1-(5,6-dimethyl-3-pyridyl)-4,4-difluoro-3,3-dimethyl-isoquinoline
I.D: 4,4-difluoro-1-[5-(fluoromethyl)-6-methyl-3-pyridyl]-3,3-dimethyl-isoquinoline
I.E: 4,4-difluoro-1-(5-methoxy-6-methyl-3-pyridyl)-3,3-dimethyl-isoquinoline
I.J: 1-(5,6-dimethyl-3-pyridyl)-4,4,5-trifluoro-3,3-dimethyl-isoquinoline
I.K: 4,4,5-trifluoro-1-[5-(fluoromethyl)-6-methyl-3-pyridyl]-3,3-dimethyl-isoquinoline
I.L: 4,4,5-trifluoro-1-(5-methoxy-6-methyl-3-pyridyl)-3,3-dimethyl-isoquinoline
I.S: 1-(5,6-dimethyl-3-pyridyl)-4,4,6-trifluoro-3,3-dimethyl-isoquinoline
I.T: 4,4,6-trifluoro-1-[5-(fluoromethyl)-6-methyl-3-pyridyl]-3,3-dimethyl-isoquinoline
I.U: 4,4,6-trifluoro-1-(5-methoxy-6-methyl-3-pyridyl)-3,3-dimethyl-isoquinoline I Furtermore the present invention relates furthermore to the compounds of the formula I

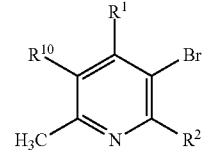

in which
if
$R^1$ is H and $R^2$ is halogen;
$R^{10}$ is $C_1$-$C_6$-alkyl and $C_1$-$C_6$-halogenalkyl; and
if
$R^1$ is H and $R^2$ is H;
$R^{10}$ is $C_1$-$C_6$-alkyl and $C_1$-$C_6$-halogenalkyl.

According to one embodiment of the invention if
$R^1$ is H and $R^2$ is halogen;
$R^{10}$ is CHs, $CH_2Cl$ and $CH_2Br$; and
if
$R^1$ is H and $R^2$ is H;
$R^{10}$ is $CH_2F$, $CH_2CH_3$, $CH_2CH(CH_3)_2$.

The invention is illustrated by the following examples:

EXAMPLE 1—BROMINATION OF 2,3-DIMETHYLPYRIDINE WITH DBDMH

To a stirred solution of 2,3-dimethylpyridine (10 g, 0.09 mol) in oleum 65% (30 mL) at 10° C.
DBDMH (14.5 g, 0.05 mol) was added. There after the exothermic reactions started. The reaction mixture was then heated at 105° C. for 2 h. After cooling to room temperature, the mixture was poured onto ice (150 g) and the ph adjusted to 12 with aqueous sodium hydroxide solution. The product was extracted into MTBE (3×100 mL), the organic phases were dried with MgSO₄ and evaporated under reduced pressure to give 5-bromo-2,3-dimethylpyridine as yellow oil (Purity acc. to GC 87.3%; yield: 83.3%.

EXAMPLE 2—BROMINATION OF 2,3-DIMETHYLPYRIDINE WITH DBDMH

To a stirred solution of 2,3-dimethylpyridine (20 g, 0.185 mol) in oleum 65% (60 mL) at 10° C. DBDMH (31.7 g, 0.11 mol) was added. There after the exothermic reactions started. The reaction mixture was then heated at 105° C. for 2 h. After cooling to room temperature, the mixture was poured onto ice (250 g) and the ph adjusted to 12 with aqueous sodium hydroxide solution. The product was extracted into MTBE (3×100 mL), the organic phases were dried with MgSO₄ and evaporated under reduced pressure to give 5-bromo-2,3-dimethylpyridine as yellow oil (34.3 g). Purity acc. to GC 87.0%; yield: 86.7%.

EXAMPLE 3—ETHYL 3,3-DIMETHYL-4H-ISOQUINOLINE-1-CARBOXYLATE

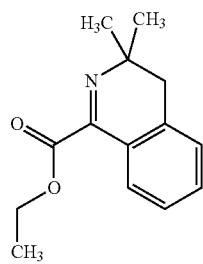 [SMILES: CCOC(=O)C1=NC(C)(C)Cc2ccccc21]

At 15° C. a solution of 380 g (2.53 mol) 2-methyl-1-phenyl-propan-2-ol and 426 g (4.3 mol) ethyl cyanoformate in 500 ml cyclohexane has been added to a mixture of 500 ml cyclohexane and 1899 g (19 mol) concentrated sulfuric acid upon stirring. After ca. 15 min the reaction mixture was poured onto an ice/water mixture and cautiously basified upon addition of concentrated NaOH-solution. The phases were separated and the aqeous layer was extracted twice with methyl-t-butylether. The combined organic phases were dried over sodium sulfate and ant volatiles were evaporated to yield 584 g (99%) ethyl 3,3-dimethyl-4H-isoquinoline-1-carboxylate as a yellow oil.

¹H-NMR (CDCl₃, δ in ppm):
7.55 (d, 1H); 7.4 (t, 1H); 7.3 (t, 1H); 7.18 (d, 1H); 4.45 (q, 2H); 2.75 (s, 2H); 1.4 (t, 3H); 1.28 (s, 6H)

EXAMPLE 4—ETHYL 4,4-DIBROMO-3,3-DIMETHYL-ISOQUINOLINE-1-CARBOXYLATE

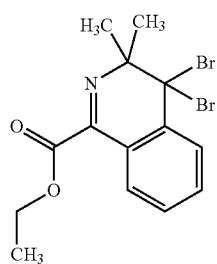 [SMILES: CCOC(=O)C1=NC(C)(C)C(Br)(Br)c2ccccc21]

20 g (86 mmol) ethyl 3,3-dimethyl-4H-isoquinoline-1-carboxylate, 33.8 g (190 mmol) N-bromo succinimide and 2.8 g azo-bis-isobutyronitrile (17 mmol) in 250 ml chloroform were heated to reflux upon stirring. After ca. 60 min HPLC showed completion of the reaction. Subsequently the reaction mixture was cooled to room temperature and diluted with 200 ml heptane. Afterwards the precipitated solid was filtered off and the mother liquor was evaporated to yield 40 g (purity 80% (HPLC), yield 95%) of the title compound ethyl 4,4-dibromo-3,3-dimethyl-isoquinoline-1-carboxylate, which was subsequently used as crude product.

HPLC-MS: HPLC-column Kinetex XB C18 1.7μ (50×2.1 mm); eluent: acetonitrile/water+0.1% TFA (5 gradient from 5:95 to 100:0 in 1.5 min at 60° C., flow gradient from 0.8 to 1.0 ml/min in 1.5 min). MS: Quadrupol Electrospray Ionisation, 80 V (positive mode).

$R_t$=1,034 min, M⁺+H=245.9 (title compound, hydrolyzed to carbonyl compound upon measurement of HPLC-MS); R=1,275, M⁺+H=389.8 (title compound ethyl 4,4-dibromo-3,3-dimethylisoquinoline-1-carboxylate)

EXAMPLE 5—ETHYL 4,4-DIFLUORO-3,3-DIMETHYL-ISOQUINOLINE-1-CARBOXYLATE

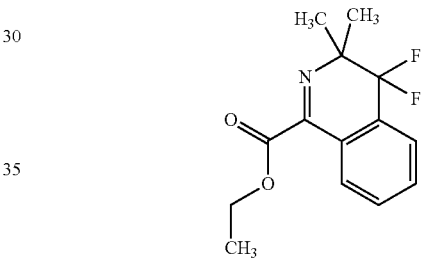

79.6 g (493 mmol) Triethylamine×3 hydrogen fluoride (NEt₃×3 HF) were added to 40 g (purity 80%, 82 mmol) ethyl 4,4-dibromo-3,3-dimethyl-isoquinoline-1-carboxylate in 100 ml acetonitrile. The mixture was heated to reflux for 2 hours, when HPLC showed completion of the reaction. Subsequently the reaction mixture was cooled to room temperature and cautiously poured onto ice cold 20% NaOH-solution. The aqueous layer was extracted twice with ethylacetate and the combined organic layers were extracted with brine. Afterwards the organic phase was dried over sodium sulfate and the volatiles were evaporated to yield 12 g (55%) of the title compound ethyl 4,4-difluoro-3,3-dimethyl-isoquinoline-1-carboxylate as brown oil.

¹H-NMR (CDCl₃, δ in ppm):
7.75 (2d, 2H); 7.65 (2t, 2H); 4.45 (q, 2H); 1.4 (m, 9H)

HPLC-MS: HPLC-column Kinetex XB C18 1.7μ (50×2.1 mm); eluent: acetonitrile/water+0.1% TFA (5 gradient from 5:95 to 100:0 in 1.5 min at 60° C., flow gradient from 0.8 to 1.0 ml/min in 1.5 min). MS: Quadrupol Electrospray Ionisation, 80 V (positive mode).

$R_t$=1,176 min, M⁺+H=268

EXAMPLE 6-(4,4-DIFLUORO-3,3-DIMETHYL-ISOQUINOLINE-1-CARBONYL)OXYLITHIUM

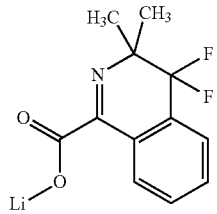

7.3 g (26 mmol) Ethyl 4,4-difluoro-3,3-dimethyl-isoquinoline-1-carboxylate and 1,143 g (27 mmol) lithium hydroxide in 100 ml methanol have been stirred at room temperature. After 2.5 hours HPLC showed total conversion of the starting material. Subsequently the solvent was evaporated at room temperature and the crystalline residue was stirred with diethylether. The crystals were filtered off and dried at 50° C. under vacuum to yield 6.3 g of the title compound as a light yellow solid (Mp>200° C., decomposition).

HPLC-MS: HPLC-column Kinetex XB C18 1.7µ (50×2.1 mm); eluent: acetonitrile/water+0.1% TFA (5 gradient from 5:95 to 100:0 in 1.5 min at 60° C., flow gradient from 0.8 to 1.0 ml/min in 1.5 min). MS: Quadrupol Electrospray Ionisation, 80 V (positive mode).

$M^+ + H = 239.9$ (Rt=0.797 min)

EXAMPLE 7-(4,4-DIFLUORO-3,3-DIMETHYL-ISOQUINOLINE-1-CARBONYL)OXYLITHIUM

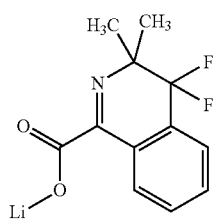

7.3 g (26 mmol) Ethyl 4,4-difluoro-3,3-dimethyl-isoquinoline-1-carboxylate and 1,143 g (27 mmol) lithium hydroxide in 100 ml methanol have been stirred at room temperature. After 2.5 hours HPLC showed total conversion of the starting material. Subsequently the solvent was evaporated at room temperature and the crystalline residue was stirred with diethylether. The crystals were filtered off and dried at 50° C. under vacuum to yield 6.3 g of the title compound as a light yellow solid (Mp>200° C., decomposition).

HPLC-MS: HPLC-column Kinetex XB C18 1.7µ (50×2.1 mm); eluent: acetonitrile/water+0.1% TFA (5 gradient from 5:95 to 100:0 in 1.5 min at 60° C., flow gradient from 0.8 to 1.0 ml/min in 1.5 min). MS: Quadrupol Electrospray Ionisation, 80 V (positive mode).

$M^+ + H = 239.9$ (Rt=0.797 min)

EXAMPLE 8-1-(5,6-DIMETHYL-3-PYRIDYL)-4,4-DIFLUORO-3,3-DIMETHYL-ISOQUINOLINE

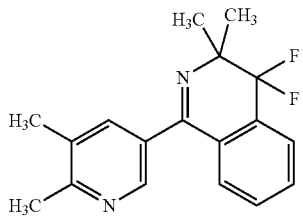

2.9 g (11.8 mmol) (4,4-Difluoro-3,3-dimethyl-isoquinoline-1-carbonyl)oxylithium and 2.0 g (10.75 mmol) 5-bromo-2,3-dimethyl-pyridine in 50 ml toluene/N-methyl-pyrrolidone 3:2 where heated at 70° C. upon stirring and a light stream of argon was passed over this mixture. Subsequently 0,231 g (1.6 mmol) copper(I)bromide and 0,145 g (0.18 mmol) Pd(dppf)Cl$_2$×CH$_2$Cl$_2$ ([1,1'-bis(diphenylphosphino)ferrocene]dichloropalladium(II), complex with dichloromethane) were added and the mixture was heated to reflux (122° C.) over night.

Afterwards the volatiles were evaporated and the residue was taken up in methyl-t-butylether This heterogenous mixture was put on top of a short silica column which was eluted with methyl-t-butylether. The combined fractions were extracted with diluted ammonia solution and lithium chloride solution. The volatiles were evaporated to yield 3.2 g (purity (HPLC) 86%, yield 85%) of the title compound as a brown oil, which crystallized upon standing.

$^1$H-NMR (CDCl$_3$, δ in ppm):

8.52 (s, 1H); 7.83 (d, 1H); 7.67 (s, 1H); 7.62 (t, 1H); 7.52, (t, 1H); 7.3 (d, 1H); 2.55 (s, 3H); 2.35 (s, 3H); 1.4 (s, 6H)

HPLC-MS: HPLC-column Kinetex XB C18 1.7µ (50×2.1 mm); eluent: acetonitrile/water+0.1% TFA (5 gradient from 5:95 to 100:0 in 1.5 min at 60° C., flow gradient from 0.8 to 1.0 ml/min in 1.5 min). MS: Quadrupol Electrospray Ionisation, 80 V (positive mode).

$M^+ + H = 301$ (R=0.889 min)

EXAMPLE 9-1-[6-(DIFLUOROMETHYL)-5-METHYL-3-PYRIDYL]-4,4-DIFLUORO-3,3-DIMETHYL-ISOQUINOLINE

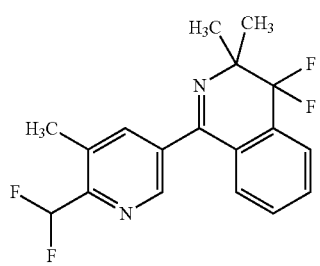 [SMILES: Cc1cc(C2=NC(C)(C)C(F)(F)c3ccccc32)cnc1C(F)F]

2.43 g (9.9 mmol) (4,4-Difluoro-3,3-dimethyl-isoquinoline-1-carbonyl)oxylithium and 2.0 g (10.75 mmol) 5-bromo-2,3-dimethyl-pyridine in 50 ml toluene/N-methyl-pyrrolidone 3:2 where heated at 70° C. upon stirring and a light stream of argon was passed over this mixture. Subsequently 0,194 g (1.35 mmol) copper(I)bromide and 0,122 g (0.15 mmol) Pd(dppf)Cl$_2$×CH$_2$Cl$_2$ ([1,1'-bis(diphenylphosphino)ferrocene]dichloropalladium(II), complex with dichloromethane) were added and the mixture was heated to reflux (122° C.) over night.

Afterwards the volatiles were evaporated and the residue was taken up in methyl-t-butylether This heterogenous mixture was put on top of a short silica column which was eluted with methyl-t-butylether. The combined fractions were extracted with diluted ammonia solution and lithium chloride solution. The volatiles were evaporated and the residue was purified via column chromatographie with heptane/methyl-t-butylether-mixtures to yield 2 g (5.9 mmol; yield 68%) of the title compound as a light brown oil.

$^1$H-NMR (CDCl$_3$, δ in ppm):
8.65 (s, 1H); 7.87 (d, 1H); 7.83 (s, 1H); 7.67 (t, 1H); 7.55 (t, 1H); 7.25, (d, 1H); 6.75 (t, 1H); 2.58 (s, 3H); 1.4 (s, 6H)

HPLC-MS: HPLC-column Kinetex XB C18 1.7µ (50×2.1 mm); eluent: acetonitrile/water+

0.1% TFA (5 gradient from 5:95 to 100:0 in 1.5 min at 60° C., flow gradient from 0.8 to 1.0 ml/min in 1.5 min). MS: Quadrupol Electrospray Ionisation, 80 V (positive mode).
M$^+$+H=337 (R$_t$=1,243 min)

EXAMPLE 10—ETHYL 4,4-DIFLUORO-3,3-DIMETHYL-ISOQUINOLINE-1-CARBOXYLATE

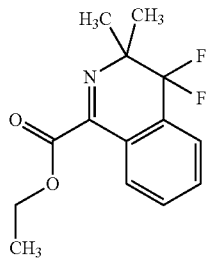

79.6 g (493 mmol) Triethylamine×3 hydrogen fluoride (NEt$_3$×3 HF) were added to 40 g (purity 80%, 82 mmol) ethyl 4,4-dibromo-3,3-dimethyl-isoquinoline-1-carboxylate in 100 ml acetonitrile. The mixture was heated to reflux for 2 hours, when HPLC showed completion of the reaction. Subsequently the reaction mixture was cooled to room temperature and cautiously poured onto ice cold 20% NaOH-solution. The aqueous layer was extracted twice with ethylacetate and the combined organic layers were extracted with brine. Afterwards the organic phase was dried over sodium sulfate and the volatiles were evaporated to yield 12 g (55%) of the title compound ethyl 4,4-difluoro-3,3-dimethyl-isoquinoline-1-carboxylate as brown oil.

$^1$H-NMR (CDCl$_3$, δ in ppm):
7.75 (2d, 2H); 7.65 (2t, 2H); 4.45 (q, 2H); 1.4 (m, 9H)

HPLC-MS: HPLC-column Kinetex XB C18 1.7µ (50×2.1 mm); eluent: acetonitrile/water+

0.1% TFA (5 gradient from 5:95 to 100:0 in 1.5 min at 60° C., flow gradient from 0.8 to 1.0 ml/min in 1.5 min). MS: Quadrupol Electrospray Ionisation, 80 V (positive mode).
R$_t$=1,176 min, M$^+$+H=268

EXAMPLE 11-1-(5,6-DIMETHYL-3-PYRIDYL)-4,4-DIFLUORO-3,3-DIMETHYL-ISOQUINOLINE

To a suspension of 5-brom-1,3-dimethylpyridine (7,805 g; 40,693 mmol) and (4,4-difluoro-3,3-dimethyl-isoquinoline-1-carbonyl)oxylithium (9,976 g; 40,693 mmol) in 100 mL of dry N-methylpyrrolidone under N$_2$ was added CuBr (875.6 mg; 6,104 mmol), Pd(dppf)Cl$_2$ (664.6 mg; 0,814 mmol) and 902.4 mg (1,628 mmol) dppf×CH$_2$Cl$_2$ ([1,1'-bis(diphenylphosphino)ferrocene]dichloropalladium(II), complex with dichloromethane). The reaction mixture was heated to 150° C. and stirred for 3 h. After the reaction was complete (H PLC) the mixture was cooled to 10° C.

Subsequently 100 ml of 5 molar hydrochloric acid was slowly added via dropping funnel. The aqueous layer was extracted twice with 100 ml n-heptane each and the organic layers were discarded.

300 ml n-Heptane was added to the aqueous layer and the solution was basified with 50% sodium hydroxide solution to pH=10 at 25° C. A solid residue precipitated which was filtered off, washed with n-heptane (3×50 ml) and discarded. Afterwards the layers were separated and the aqueous layer was extracted with n-heptane (2×300 mL). The combined organic layers were dried over Na$_2$SO$_4$, the drying agent was filtered off and the volatiles were evaporated to obtain 11.1 g of the title compound as orange crystals.

Recrystallisation from heptane yielded 8.05 g beige crystals (purity 93.5% (quant. $^1$H-NMR), yield 61.6%). Purification via column chromatography with cyclohexane/ethyl acetate mixtures afforded 1-(5,6-dimethyl-3-pyridyl)-4,4-difluoro-3,3-dimethyl-isoquinoline as white crystals, mp=104-105° C.

$^1$H-NMR (CDCl$_3$, δ in ppm):
8.52 (s, 1H); 7.83 (d, 1H); 7.67 (s, 1H); 7.62 (t, 1H); 7.52, (t, 1H); 7.3 (d, 1H); 2.55 (s, 3H); 2.35 (s, 3H); 1.4 (s, 6H)

EXAMPLE 12-1-[6-(DIFLUOROMETHYL)-5-METHYL-3-PYRIDYL]-4,4-DIFLUORO-3,3-DIMETHYL-ISOQUINOLINE

To a suspension of 5-bromo-2-(difluoromethyl)-3-methyl-pyridine (36.59 g; 163.16 mmol) and (4,4-difluoro-3,3-dimethyl-isoquinoline-1-carbonyl)oxylithium (40.00 g; 163,165 mmol) in 480 ml of dry N-methylpyrrolidone under N$_2$ were added CuBr (3.51 g; 24.48 mmol), Pd(dppf)Cl$_2$× CH$_2$Cl$_2$ (2.67 g; 3.26 mmol) and 3.62 g (6.53 mmol) dppf ([1,1'-bis(diphenylphosphino)ferrocene]dichloropalladium (II), complex with dichloromethane). The reaction mixture was heated at 150° C. and stirred for 8 h. After the reaction was complete (HPLC) the mixture was cooled to 10° C. and subsequently added to a mixture of 300 ml water and 500 ml n-heptane. Afterwards the mixture was basified with 50 ml of 25% ammonia-solution at 25° C. (pH 11-12) and filtered over Celite. The Celite was washed with n-heptane and the aqueous ammonia layer was separated from the n-hexane layer.

The combined heptane phases were washed twice with 250 ml of 5% hydrochloric acid. After the first extraction some insoluble material precipitated which was filtered off and discarded. The organic layer was dried over Na$_2$SO$_4$, filtered and evaporated to obtain 40.5 g of the title compound (purity ~80% (quant.-HPLC)).

This product was dissolved in 400 ml of n-heptane. The heptane-phase was extracted twice with 250 ml of 15% HCl and the heptane phase was discarded afterwards.

The combined HCl-layers were treated three times with 500 ml of dichloromethane to extract the product into the organic phase.

Thereafter the combined dichloromethane layers were stirred for 1 h with 300 ml of 20% Na$_2$CO$_3$-solution.

The phases were separated and the organic layer was dried over Na$_2$SO$_4$, filtered and evaporated to obtain 33.3 g 1-[6-(Difluoromethyl)-5-methyl-3-pyridyl]-4,4-difluoro-3,3-dimethylisoquinoline (purity 92.5% (quant. $^1$H-NMR), yield 56%).

The title compound could be further purified via column chromatography with cyclohexane/ethyl acetate mixtures.

$^1$H-NMR (CDCl$_3$, δ in ppm):

8.65 (s, 1H); 7.87 (d, 1H); 7.83 (s, 1H); 7.67 (t, 1H); 7.55 (t, 1H); 7.25, (d, 1H); 6.75 (t, 1H); 2.58 (s, 3H); 1.4 (s, 6H)

The invention claimed is:

1. A process for preparing a compound of formula I,

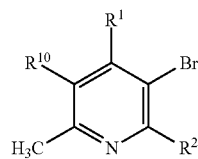

in which
- $R^1$ is in each case independently selected from hydrogen, halogen, $C_1$-$C_6$-alkyl and $C_1$-$C_6$-halogenalkyl;
- $R^2$ is in each case independently selected from hydrogen and halogen;
- $R^{10}$ is in each case independently selected from H, halogen, O($R^{95}$), $C_1$-$C_6$-alkyl and $C_1$-$C_6$-halogenalkyl; wherein
- $R^{95}$ is $C_1$-$C_6$-alkyl, $C_1$-$C_6$-halogenalkyl;

comprising:
(i) reacting a compound of formula II

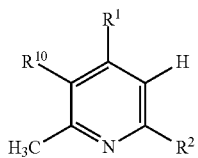

wherein $R^1$, $R^2$ and $R^{19}$ are as defined above with 1,3-dibromo-5,5-dimethylhydantoin (DBDMH) in the presence of oleum 65%.

2. The process according to claim 1, wherein $R^1$ and $R^2$ are hydrogen, and $R^{10}$ is $C_1$-$C_6$-alkyl.

3. The process according to claim 1, wherein $R^1$ and $R^2$ are hydrogen and $R^{10}$ is CH$_3$.

4. A process for preparing 2,3-disubstituted pyridine compounds of the formula III

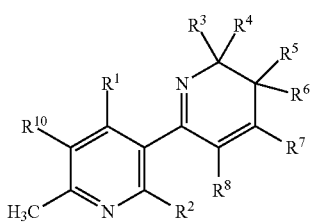

wherein
- $R^1$ is in each case independently selected from hydrogen, halogen, $C_1$-$C_6$-alkyl and $C_1$-$C_6$-halogenalkyl;
- $R^2$ is in each case independently selected from hydrogen and halogen;
- $R^3$, $R^4$ are independently selected from $C_1$-$C_6$-alkyl, $C_2$-$C_6$-alkenyl, $C_2$-$C_6$-alkynyl, $C_1$-$C_6$-halogenalkyl, $C_2$-$C_6$-halogenalkenyl and $C_2$-$C_6$-halogenalkynyl;
- $R^5$ is halogen;
- $R^6$ is halogen;
- $R^7$, $R^8$ together with the carbon atoms to which they are bound form a ring A, wherein the ring A is phenyl and wherein the ring A is substituent by $(A^{76})_o$, wherein
  is 0, 1, 2 or 3; and
- $R^{78}$ is independently selected from halogen, $C_1$-$C_6$-alkyl, $C_1$-$C_6$-alkoxy, $C_1$-$C_6$-halogenalkyl and $C_1$-$C_6$-halogenalkoxy;
- $R^{10}$ is in each case independently selected from H, halogen, O($R^{95}$), $C_1$-$C_6$-alkyl and $C_1$-$C_6$-halogenalkyl; wherein
- $R^{95}$ is $C_1$-$C_6$-alkyl, $C_1$-$C_6$-halogenalkyl;

comprising:
(i) providing a compound of the formula I by a process according to claim 1;
(ii) reacting the compound of the formula I with a compound of the formula IV

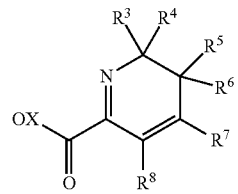

in which
- $R^3$, $R^4$, $R^5$, $R^6$, $R^7$ and $R^8$ are each as defined for formula III; and X is a metal ion.

5. The process according to claim 4, wherein $R^1$ and $R^2$ are hydrogen, $R^3$ and $R^4$ is $C_1$-$C_6$-alkyl, $R^5$ and $R^6$ are halogen, $R^7$ and $R^8$ form a phenyl, o is 0 and $R^{10}$ is $C_1$-$C_6$-alkyl.

6. The process according to claim 4, wherein $R^1$ and $R^2$ are hydrogen, $R^3$ and $R^4$ are CH$_3$, $R^5$ and $R^6$ are F, $R^7$ and $R^8$ form a phenyl, o is 0 and $R^{10}$ is CH$_3$.

7. The process according to claim 4, wherein X is selected from the group consisting of Li, Na, K, and Cs.

* * * * *